(12) United States Patent
Lai

(10) Patent No.: US 9,772,079 B2
(45) Date of Patent: Sep. 26, 2017

(54) FLAME SIMULATING DEVICE HAVING AN OSCILLATING DEVICE TO VAPORIZE LIQUID

(71) Applicant: Wen-Cheng Lai, Taoyuan (TW)

(72) Inventor: Wen-Cheng Lai, Taoyuan (TW)

(*) Notice: Subject to any disclaimer, the term of this patent is extended or adjusted under 35 U.S.C. 154(b) by 27 days.

(21) Appl. No.: 14/882,886

(22) Filed: Oct. 14, 2015

(65) Prior Publication Data
US 2017/0108188 A1   Apr. 20, 2017

(51) Int. Cl.
| F21S 10/04 | (2006.01) |
| F21S 6/00 | (2006.01) |
| A61L 9/00 | (2006.01) |
| F21W 121/00 | (2006.01) |
| F21Y 115/10 | (2016.01) |

(52) U.S. Cl.
CPC .............. *F21S 10/046* (2013.01); *A61L 9/00* (2013.01); *F21S 6/001* (2013.01); *F21W 2121/00* (2013.01); *F21Y 2115/10* (2016.08)

(58) Field of Classification Search
CPC ........ F21S 10/04; F21S 10/043; F21S 10/046; F21Y 2101/02; F21Y 2115/10; A61L 9/00
See application file for complete search history.

(56) References Cited

U.S. PATENT DOCUMENTS

| 6,220,720 B1 * | 4/2001 | Stephens .................. F21L 7/00 362/205 |
| 7,093,949 B2 * | 8/2006 | Hart ..................... A01M 1/2033 362/253 |
| 7,503,668 B2 * | 3/2009 | Porchia .................. A01M 1/02 362/161 |
| 9,052,078 B2 * | 6/2015 | Sheng .................. F21S 10/046 |
| 9,625,112 B2 * | 4/2017 | Li ............................ A61L 9/03 |
| 2008/0036332 A1 * | 2/2008 | Helf ......................... A61L 9/12 310/311 |
| 2016/0298816 A1 * | 10/2016 | Fang ..................... F21S 10/046 |
| 2016/0363280 A1 * | 12/2016 | Angelotti ............... F21S 10/04 |

* cited by examiner

*Primary Examiner* — Robert May
(74) *Attorney, Agent, or Firm* — C. G. Mersereau; Nikolai & Mersereau, P.A.

(57) ABSTRACT

A flame simulating device includes an upper part, a light source, a container and an oscillation device. The upper part has a flame element which freely swings relative to the upper part, and the light source located in the upper part emits light toward the flame-shaped portion. The container is located below the upper part and contains liquid therein. The oscillation device is located at the underside of the container and oscillates the liquid in the container to generate liquid vapor and liquid droplets, the liquid droplets hit and irregularly swing the flame element. The liquid vapor provides a foggy environment.

18 Claims, 8 Drawing Sheets

FLAME SIMULATING DEVICE HAVING AN OSCILLATING DEVICE TO VAPORIZE LIQUID

BACKGROUND OF THE INVENTION

1. Fields of the Invention

The present invention relates to a flame simulating device, and more particularly, to a flame simulating device that simulates a real candle frame.

2. Descriptions of the Prior Art

Although conventional illumination tools, such as candles, oil lamps or the like, have been replaced by various electric lamps, the candles or the oil lamps still have specific meanings and distinctive visual effects in some special occasions or special situations, and thus cannot be replaced by the illumination lamps used in the today's daily life. For example, upon worshiping deities or ancestors, incense and candles are often used, and the beating fire on the candle is used to anchor the reminiscence on the ancestor and the endless longing to the posterity. In some occasions where specific atmospheres need to be created, the fire beating effect of the burning candle is also advantageous to the generation of different visual enjoyments. However, the conventional lamps, such as candles, oil lamps or the like, are used for illumination by way of flame combustion, and have the predetermined security risks. When the candles or oil lamps are upset due to the wind blowing or the artificial inadvertent touch, the ambient flammable objects tend to be ignited to cause the fire accident. Thus, simulated lamps for simulating candle illumination effects have been developed.

There are different types of lamps capable of simulating frames of candles and generally include a case shaped as a candle, yellowish light is protected to an object, or a flame-shaped plate is illuminated to show the effect of using a candle. Some developers even use a driving device to drive the flame-shaped plate to swing back and forth to more simulate a real movement of the candle flame. However, the flame-shaded plate has a fixed swing mode which is different from the dynamic visual effect of the real flame of a candle.

The present invention intends to provide a flame simulating device to eliminate the shortcomings mentioned above.

SUMMARY OF THE INVENTION

The present invention relates to a flame simulating device and comprises an upper part having a flame element which freely swings relative to the upper part, and the flame element has a flame-shaped portion located above the upper part. A light source is located in the upper part and emits light toward the flame-shaped portion.

A container is located below the upper part and contains liquid therein. An oscillation device is located at the underside of the container to oscillate the liquid in the container to generate liquid droplets which hit and swing the flame element.

Preferably, the light source includes a Light Emitting Diode (LED) with two LED chips which generate alternative and flashing light beams toward the flame element.

Preferably, the upper part is connected to a cover which is detachably mounted to a top opening of the container. A first room is defined between the container and the cover.

Preferably, the oscillation device is an ultra-sonic oscillation device which oscillates the liquid into liquid vapor which is released from an exhaust hole defined through the upper part.

Preferably, the container has an extension portion at the underside thereof. The extension portion is connected to a base, and a second room is defined between the extension portion and the base.

Preferably, a case is mounted to the container and the cover. A third room is defined between the case, the container and the cover. The case is detachably connected to the base and has a positioning hole with which the upper part is engaged.

Preferably, the base has a ventilation hole, a blowing unit is located relative to the ventilation hole for introducing outside air into the second room. The extension portion has a communication hole which communicates between the second room and the third room. The cover has an air inlet for introducing air in the third room into the first room and flowing out via the exhaust hole.

Preferably, a conductive unit is connected between the container and the cover.

Preferably, the conductive unit has a metal part and a metal resilient plate which is in contact with the metal part when the cover is mounted to the container.

Preferably, the oscillation device is electrically connected to a control device. The light source is electrically connected to the control device via the conductive unit.

Preferably, the flame element has an impact plate connected to the underside thereof.

The primary object of the present invention is to provide a flame simulating device which makes the flame element to irregularly swing and the liquid vapor provides a foggy environment.

Another object of the present invention is to provide a flame simulating device which provides flashing light to illuminate the irregularly swinging flame element so as to create an environment with a highly simulated candle flame.

The present invention will become more obvious from the following description when taken in connection with the accompanying drawings which show, for purposes of illustration only, a preferred embodiment in accordance with the present invention.

DETAILED DESCRIPTION OF THE PREFERRED EMBODIMENT

Figure 1:
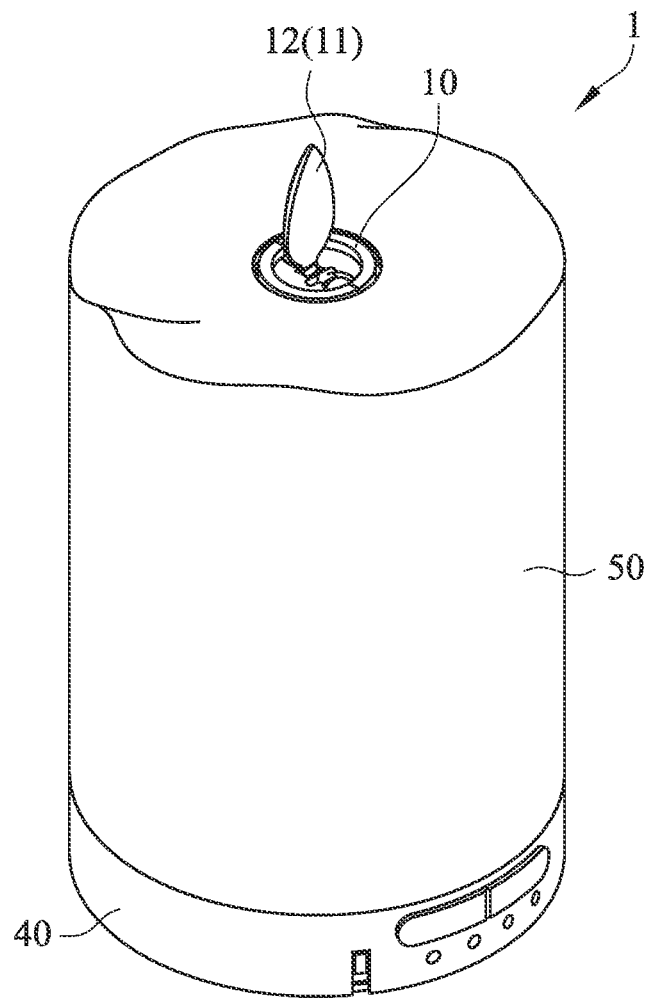
FIG. 1 is a perspective view to show the flame simulating device of the present invention.
Figure 2:
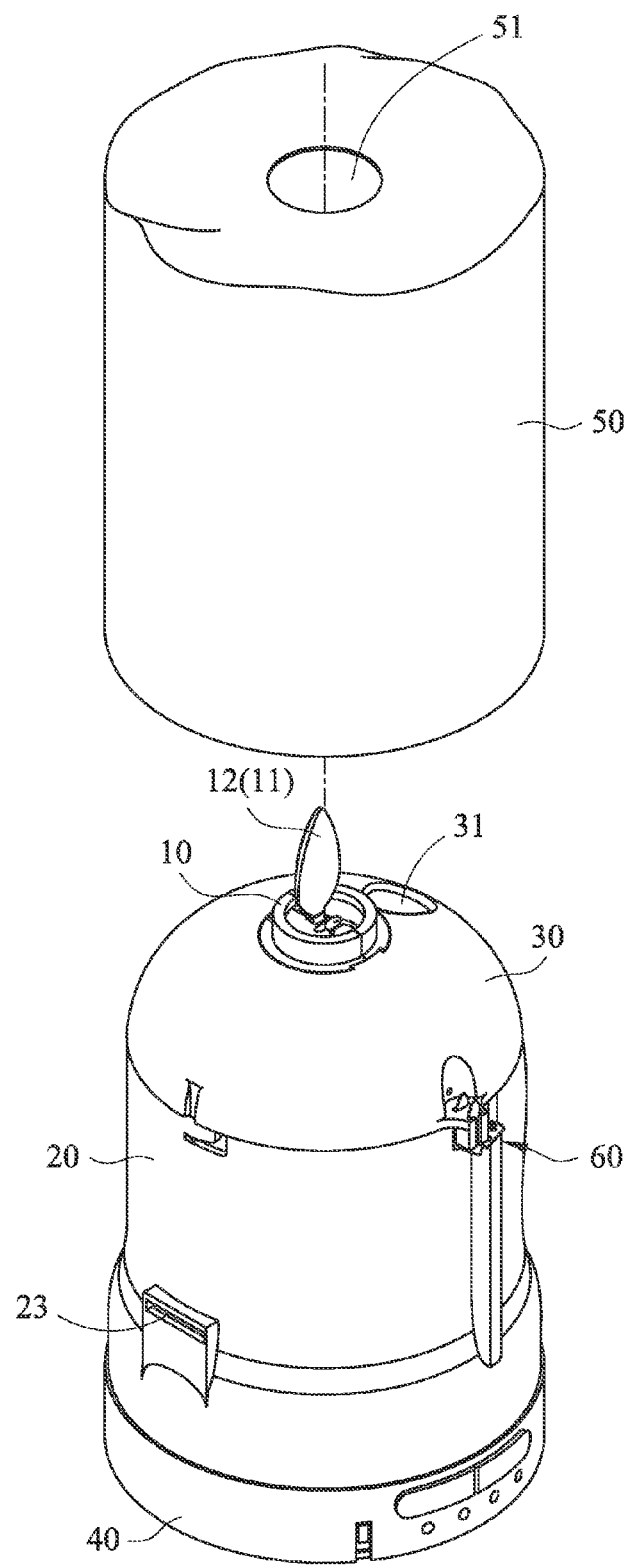
FIG. 2 shows that the case is to be mounted to the flame simulating device of the present invention.
Figure 3:
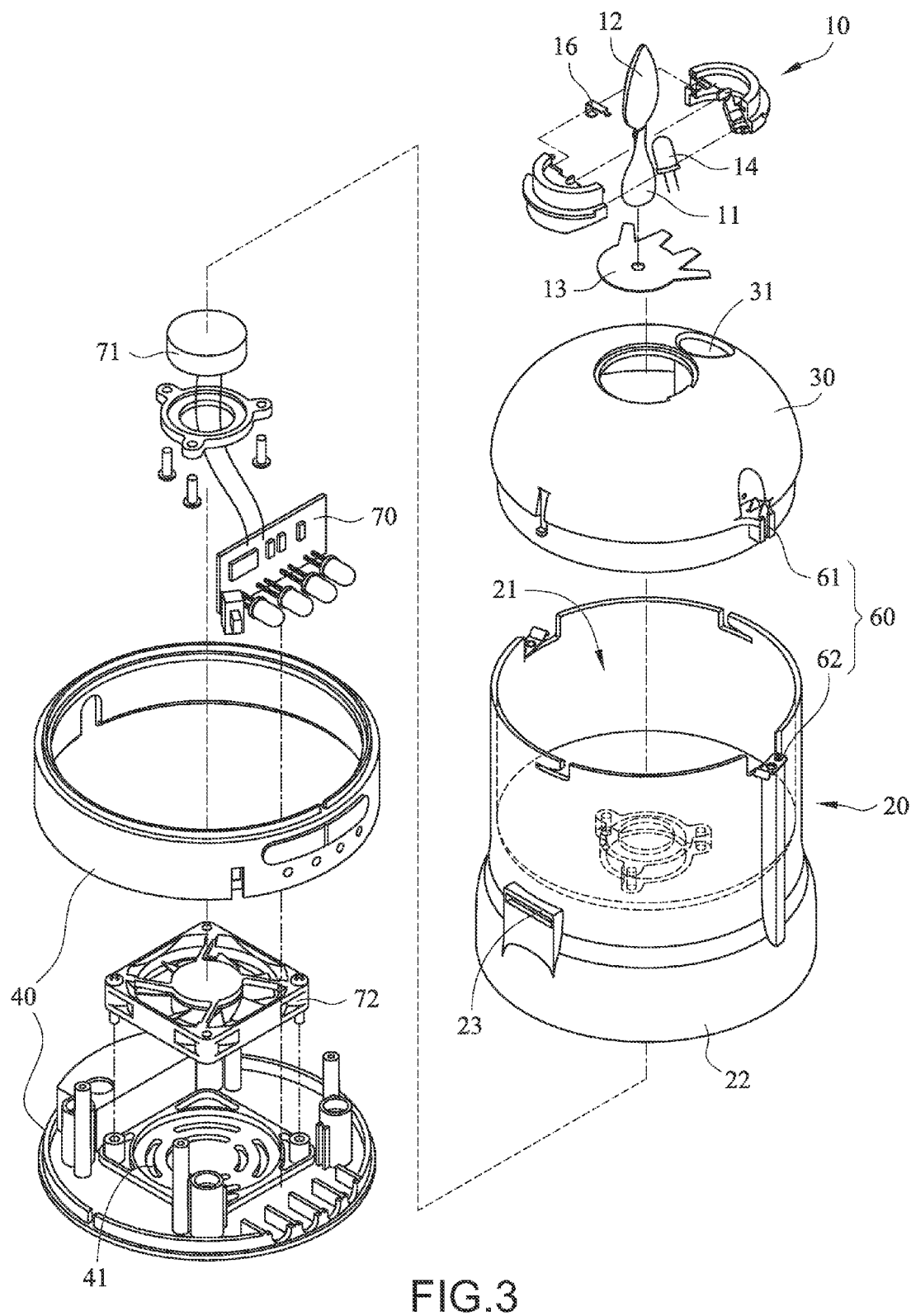
FIG. 3 is an exploded view to show the flame simulating device of the present invention.

Referring to FIGS. 1 to 4, the flame simulating device 1 of the present invention comprises an upper part 10, a container 20, a cover 30, a base 40 and a case 50. The upper part 10 has a hook 16 and a light source 14 located therein. A flame element 11 is hanged at one end of the hook 16, the flame element 11 freely swings relative to the upper part 10 due to proper weight center arrangement. The flame element 11 has a flame-shaped portion 12 formed at the top section thereof and located above the upper part 10. The light source 14 emits light toward the flame-shaped portion 12.

The upper part 10 is located at the top portion of the cover 30 which is detachably mounted to a top opening 21 of the container 20. The container 20 contains liquid such as water therein and the oscillation device 71 is installed at the underside of the container 20. The oscillation device 71 oscillates the liquid in the container 20 to generate liquid vapor and liquid droplets, wherein the liquid droplets hit and irregularly swing the flame element 11. In one embodiment, the flame element 11 has an impact plate 13 connected to the underside thereof so as to provide a larger impact area to the liquid droplets. The impact plate 13 enhances the swinging action of the flame element 11 and also performs a restriction member to restrict the liquid droplets from splashing out.

Figure 5:
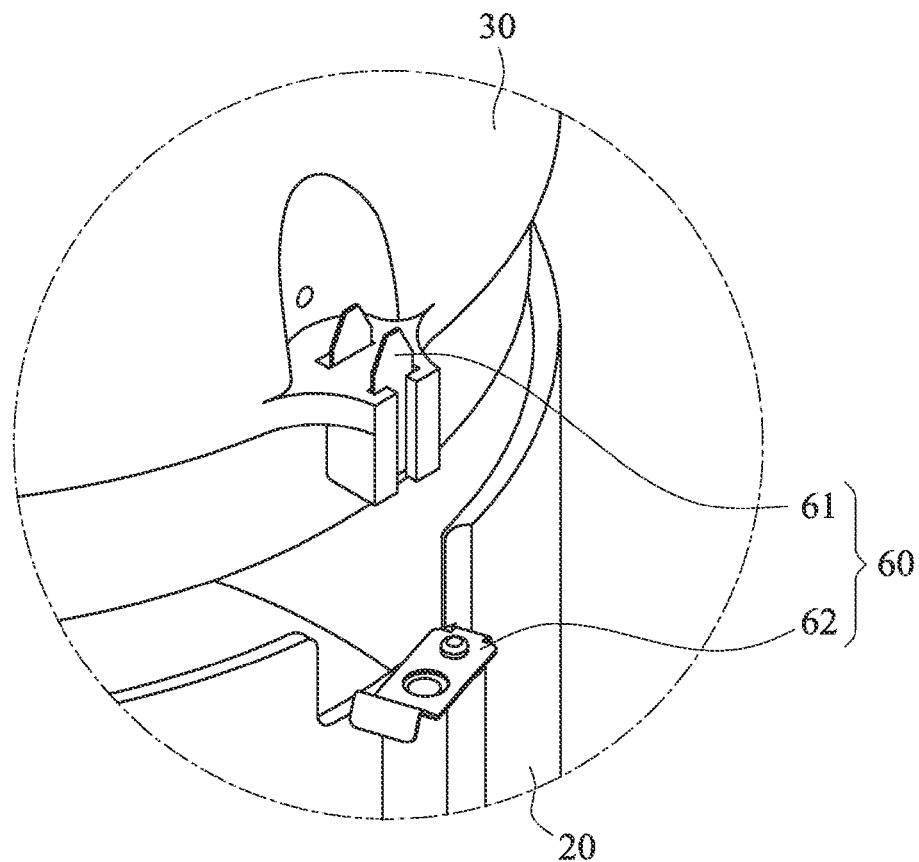
FIG. 5 shows the conductive unit connected between the cover and the container of the present invention.

The container 20 has an extension portion 22 connected to the underside thereof, the extension portion 22 is connected to the base 40. The base 40 has a control device 70 and a blowing unit 72 received therein. The control unit 70 is electrically connected to the oscillation device 71 at the underside of the container 20, the operation panel on the outside of the base 40, the power supply and the light source 14. A conductive unit 60 is connected between the container 20 and the cover 30 so that when the cover 30 is mounted to the container 20, a circuit loop is formed to electrically connect the light source 14 to the control device 70. As shown in FIG. 5, the conductive unit 60 has a metal part 61 on the cover 30, and a metal resilient plate 62 on the container 20. The metal part 61 is connected to the light source 14, and the metal resilient plate 62 is connected to the control device 70. When the cover 30 is mounted to the container 20, the metal part 61 is in contact with the metal resilient plate 62.

Figure 4:
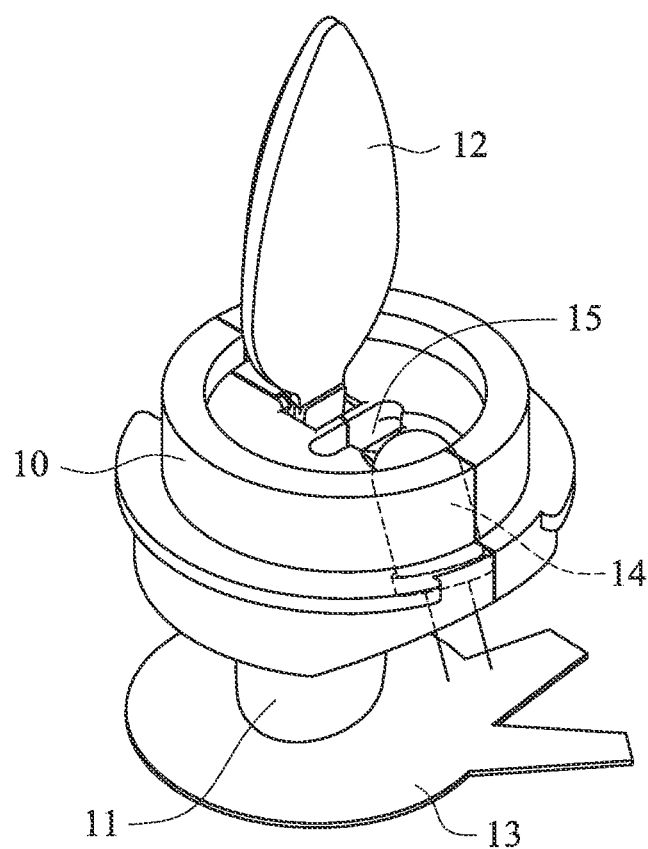
FIG. 4 is a perspective view to show the upper part and the flame element of the present invention.

The case 50 is made to be shaped as a candle and detachably connected to the base 40. The case 50 is mounted to the container 20 and the cover 30. The case 50 has a positioning hole 51 with which the upper part 10 is engaged so that the flame-shaped portion 12 of the flame element 11 is exposed beyond the case 50. As shown in FIG. 4, an exhaust hole 15 is defined in the upper part 10 and located beside the flame element 11. The oscillation device 71 is an ultra-sonic oscillation device which oscillates the liquid into the liquid vapor and liquid droplets, wherein the liquid droplets hit the impact plate 13, and the liquid vapor is released from the exhaust hole 15 to simulate the smoke of the burning flame.

Figure 6:
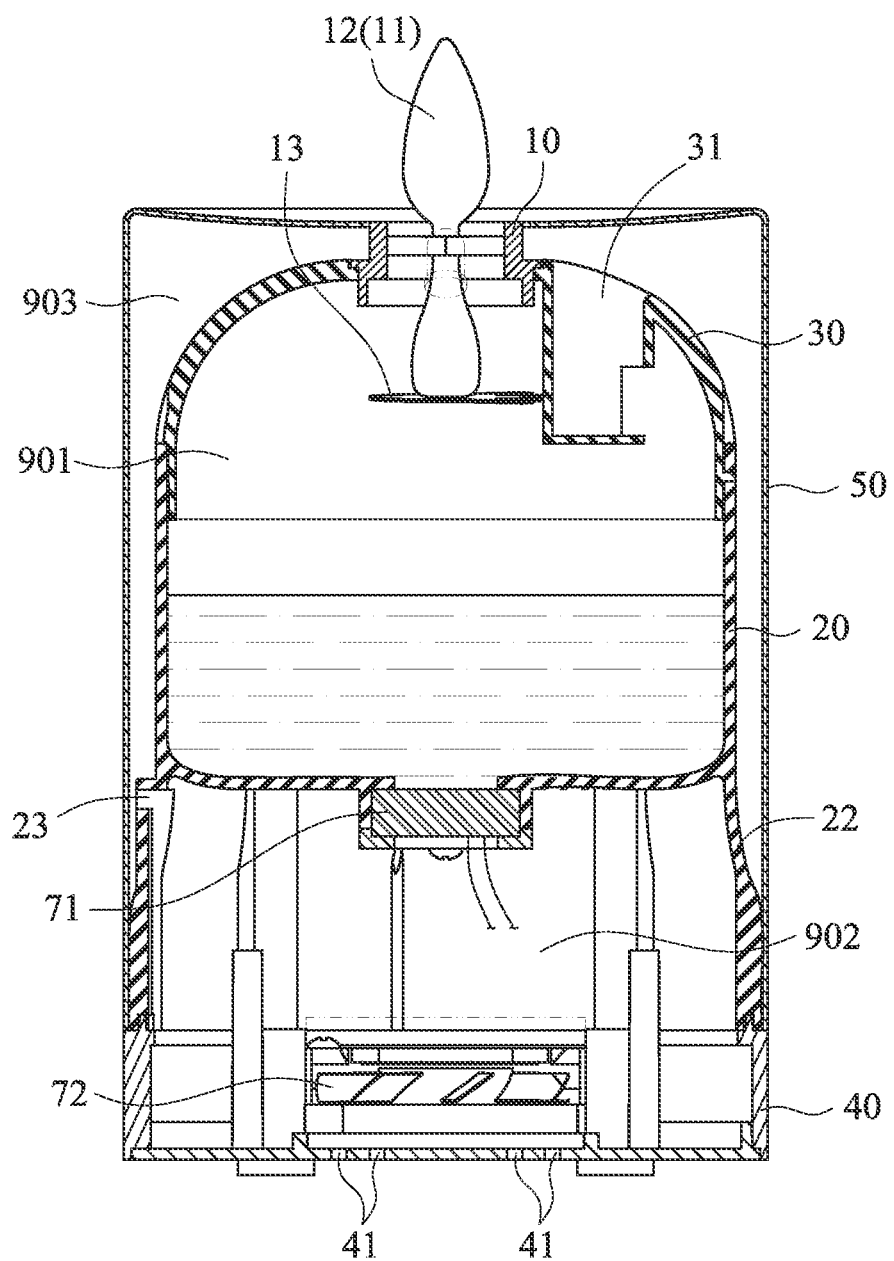
FIG. 6 is a cross sectional view showing the flame simulating device of the present invention.

In one embodiment, the light source 14 includes a Light Emitting Diode (LED) with two LED chips which generate alternative and flashing light beams toward the flame element 11. As shown in FIG. 6, a first room 901 is defined between the container 20 and the cover 30. A second room 902 is defined between the extension portion 22 and the base 40. A third room 903 is defined between the case 50, the container 20 and the cover 30. The base 40 has a ventilation hole 41 and the blowing unit 72 is located relative to the ventilation hole 41 for introducing outside air into the second room 902. The extension portion 22 has a communication hole 23 which communicates between the second room 902 and the third room 903. The cover 30 has an air inlet 31 for introducing the air in the third room 903 into the first room 901 and flowing out via the exhaust hole 15. The blowing unit 72 controls the air flow direction to release the foggy liquid vapor and the air via the exhaust hole 15.

Figure 7:
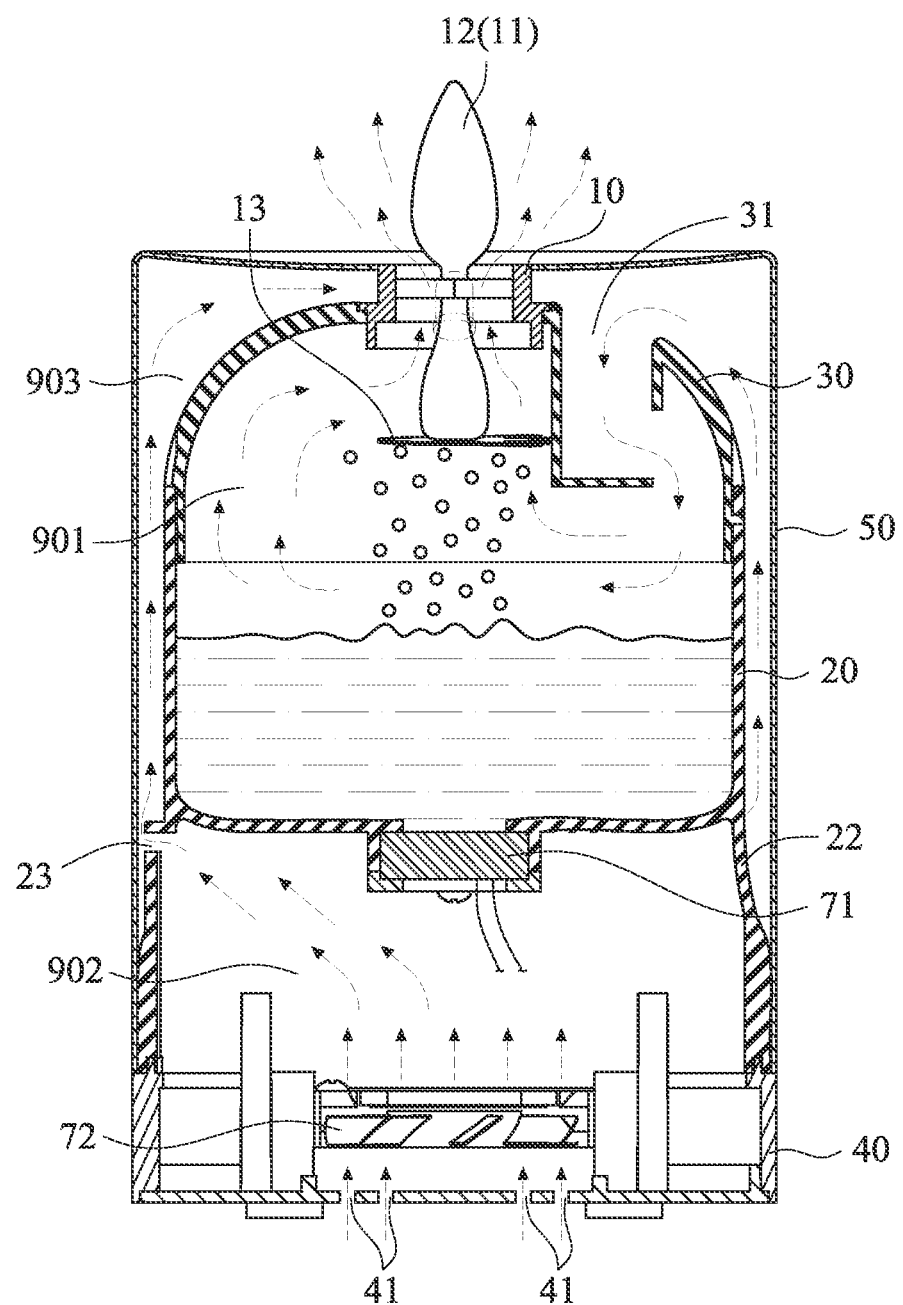
FIG. 7 is a cross sectional view to show the operation of the flame simulating device of the present invention.
Figure 8:
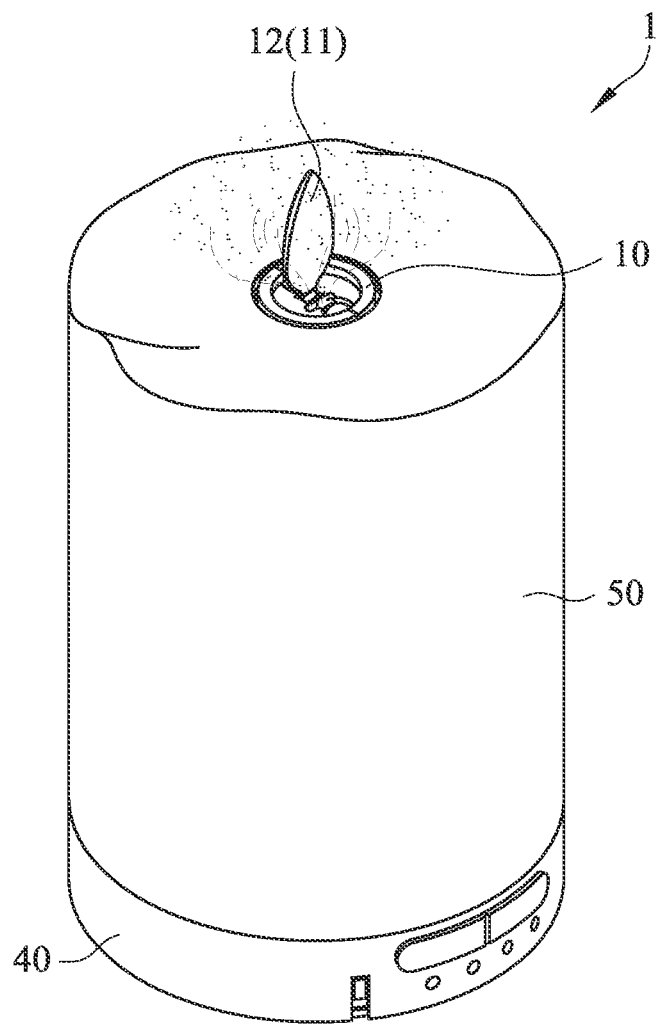
FIG. 8 is a perspective view to show the operation of the flame simulating device of the present invention.

As shown in FIGS. 7 and 8, when in use, the control device 70 activates the light source 14, the oscillation device 71 and the blowing unit 72. The light source 14 generates flashing and alternative light toward the flame element 11, and the oscillation device 71 oscillates the liquid in the container 20 into the liquid droplets and liquid vapor, the liquid droplets hit the flame element 11 which irregularly swings. The blowing unit 72 introduces outside air into the second room 902 via the ventilation hole 41, and the air then flows out from the communication hole 23 and enters into the third room 903. The air in the third room 903 flows into the first room 901 via the air inlet 31 to drive the air in the first room 901 to be released from the exhaust hole 15. The liquid vapor together with the air makes the swinging flame element 11 like a real candle flame.

The liquid in the container 20 can also be aromatic oil or any suitable liquid.

While we have shown and described the embodiment in accordance with the present invention, it should be clear to those skilled in the art that further embodiments may be made without departing from the scope of the present invention.

What is claimed is:

1. A flame simulating device comprising:
    an upper part having a flame element which freely swings relative to the upper part, the flame element having a flame-shaped portion located above the upper part;
    a light source located in the upper part and emitting light toward the flame-shaped portion;
    a container located below the upper part, the upper part connected to a cover which is detachably mounted to a top opening of the container, a first room defined between the container and the cover, liquid received in the container, and
    an oscillation device located at an underside of the container, the oscillation device being an ultra-sonic oscillation device which oscillates the liquid into liquid vapor and liquid droplets, the liquid vapor released from an exhaust hole defined through the upper part, the liquid droplets hitting and swinging the flame element.

2. The flame simulating device as claimed in claim 1, wherein the light source includes a Light Emitting Diode (LED) with two LED chips which generate alternative and flashing light beams toward the flame element.

3. The flame simulating device as claimed in claim 2, wherein the upper part is connected to a cover which is detachably mounted to a top opening of the container, a first room is defined between the container and the cover.

4. The flame simulating device as claimed in claim 3, wherein the oscillation device is an ultra-sonic oscillation device which oscillates the liquid in the container into liquid vapor which is released from an exhaust hole defined through the upper part.

5. The flame simulating device as claimed in claim 4, wherein the container has an extension portion connected to an underside thereof, the extension portion is connected to a base, a second room is defined between the extension portion and the base.

6. The flame simulating device as claimed in claim 5, wherein a case is mounted to the container and the cover, a third room is defined between the case, the container and the cover, the case is detachably connected to the base and has a positioning hole with which the upper part is engaged.

7. The flame simulating device as claimed in claim 6, wherein the base has a ventilation hole, a blowing unit is located relative to the ventilation hole for introducing outside air into the second room, the extension portion has a communication hole which communicates between the second rom and the third room, the cover has an air inlet for introducing air in the third room into the first room and flowing out via the exhaust hole.

8. The flame simulating device as claimed in claim 7, wherein the flame element has an impact plate connected to an underside thereof.

9. The flame simulating device as claimed in claim 3, wherein a conductive unit is connected between the container and the cover.

10. The flame simulating device as claimed in claim 9, wherein the conductive unit has a metal part and a metal resilient plate which is in contact with the metal part when the cover is mounted to the container.

11. The flame simulating device as claimed in claim 9, wherein the oscillation device is electrically connected to a control device, the light source is electrically connected to the control device via the conductive unit.

12. The flame simulating device as claimed in claim 1, wherein the container has an extension portion at an underside thereof, the extension portion is connected to a base, a second room is defined between the extension portion and the base.

13. The flame simulating device as claimed in claim 12, wherein a case is mounted to the container and the cover, a third room is defined between the case, the container and the cover, the case is detachably connected to the base and has a positioning hole with which the upper part is engaged.

14. The flame simulating device as claimed in claim 13, wherein the base has a ventilation hole, a blowing unit is located relative to the ventilation hole for introducing outside air into the second room, the extension portion has a communication hole which communicates between the second room and the third room, the cover has an air inlet for introducing air in the third room into the first room and flowing out via the exhaust hole.

15. The flame simulating device as claimed in claim 1, wherein a conductive unit is connected between the container and the cover.

16. The flame simulating device as claimed in claim 15, wherein the conductive unit has a metal part and a metal resilient plate which is in contact with the metal part when the cover is mounted to the container.

17. The flame simulating device as claimed in claim 15, wherein the oscillation device is electrically connected to a control device, the light source is electrically connected to the control device via the conductive unit.

18. The flame simulating device as claimed in claim 1, wherein the flame element has an impact plate connected to an underside thereof.

* * * * *